United States Patent
Kimura et al.

(10) Patent No.: US 8,808,728 B2
(45) Date of Patent: Aug. 19, 2014

(54) FEED ADDITIVE FOR LAYING HEN AND FEED CONTAINING THE SAME

(75) Inventors: Takashi Kimura, Uji (JP); Munehiko Dombo, Uji (JP)

(73) Assignee: Unitika Ltd., Hyogo (JP)

( * ) Notice: Subject to any disclaimer, the term of this patent is extended or adjusted under 35 U.S.C. 154(b) by 770 days.

(21) Appl. No.: 12/574,779

(22) Filed: Oct. 7, 2009

(65) Prior Publication Data

US 2010/0022463 A1      Jan. 28, 2010

Related U.S. Application Data

(62) Division of application No. 10/587,945, filed as application No. PCT/JP2005/001592 on Feb. 3, 2005, now abandoned.

(30) Foreign Application Priority Data

Feb. 6, 2004    (JP) .................................. 2004-030898

(51) Int. Cl.
*A23K 1/17*     (2006.01)
*A23K 1/165*    (2006.01)
*A23K 1/18*     (2006.01)

(52) U.S. Cl.
CPC .................................... *A23K 1/1826* (2013.01)
USPC .................................................... 424/442

(58) Field of Classification Search
CPC .................................................. A23K 1/1826
USPC ................................................... 424/442
See application file for complete search history.

(56) References Cited

U.S. PATENT DOCUMENTS

| | | | |
|---|---|---|---|
| 2,746,916 A | | 5/1956 | Magariello |
| 3,754,084 A | * | 8/1973 | Fujie et al. ...................... 514/30 |
| 5,133,963 A | * | 7/1992 | Ise .............................. 424/94.61 |
| 2001/0046484 A1 | | 11/2001 | Maruta et al. |
| 2003/0068359 A1 | * | 4/2003 | Register ........................ 424/442 |

FOREIGN PATENT DOCUMENTS

| | | |
|---|---|---|
| DE | 2547181 | 4/1977 |
| EP | 1452097 | 9/2004 |
| JP | 1-285158 | 11/1989 |
| JP | 371101 B2 | 11/1991 |
| JP | 07-147910 | 10/1995 |
| JP | 07-277990 | 10/1995 |
| JP | 07-277991 | 10/1995 |
| JP | 9-28309 | 2/1997 |
| JP | 9-47232 | 2/1997 |

(Continued)

OTHER PUBLICATIONS

Saarela (International Dairy Journal, vol. 13, Issue 4, 2003, pp. 291-302).*

(Continued)

*Primary Examiner* — Benjamin Packard
(74) *Attorney, Agent, or Firm* — Sughrue Mion, PLLC

(57) ABSTRACT

A feed additive for laying hens comprising lactobionic acid or a lactobionic acid salt and a feed characterized by containing a feed additive for laying hens comprising lactobionic acid or a lactobionic acid salt and a feed. Namely, a feed additive for laying hens, which is excellent in effect of reinforcing eggshells, shows a particularly remarkable effect of improving eggshell qualities in the second half of the laying period, relieves stress caused by forced molting, cage transfer and so on and can inhibit lowering in the egg-laying rate.

9 Claims, 1 Drawing Sheet

(56) References Cited

FOREIGN PATENT DOCUMENTS

| JP | 1018628 A | 4/1998 |
| JP | 2001-95499 | 4/2001 |
| JP | 2001-245657 | 9/2001 |
| JP | 2002-520003 | 7/2002 |
| WO | 02/058483 | 8/2002 |

OTHER PUBLICATIONS

Brommage et al (Intestinal calcium absorption in rats is stimulated by dietary lactulose and other resistant sugars. 1993. Journal of Nutrition 123, 2186-2194).*

European Search Report issued on Oct. 15, 2010, in the corresponding European Patent Application No. 05709685.1.

Chinese First Office Action for Application No. 2005-80004276.6, issued Jun. 26, 2009.

English Abstracts from the EPO Website of the IDS documents.

Rivera et al., Bioavailability of iron- and copper-supplemented milk for Mexican school children, Am. J. of Clinical Nutrition., 36:1162-1169 (1982).

European Office Action in counterpart European Application No. 05 709 685.1-1221, dated Feb. 18, 2010.

Office Action issued Sep. 6, 2011 from the Japanese Patent Office in counterpart Japanese application 2005517722.

Supplementary Partial European Search Report for EP 05709685, dated Jun. 16, 2009.

International Search Report for PCT/JP2005/001592, dated May 17, 2005.

Communication dated Jun. 5, 2012 issued by the Japanese Patent Office in Japanese Application No. 2005-517722, pub date 2012.

An Amendment for formality and English translation submitted in corresponding Japenese Patent Application No. 2005-517722; 16 pages total, 2012.

A Certified Experiment Results and English translation submitted in corresponding Japanese Patent Application No. 2005-517722; 4 pages total, 2012.

* cited by examiner

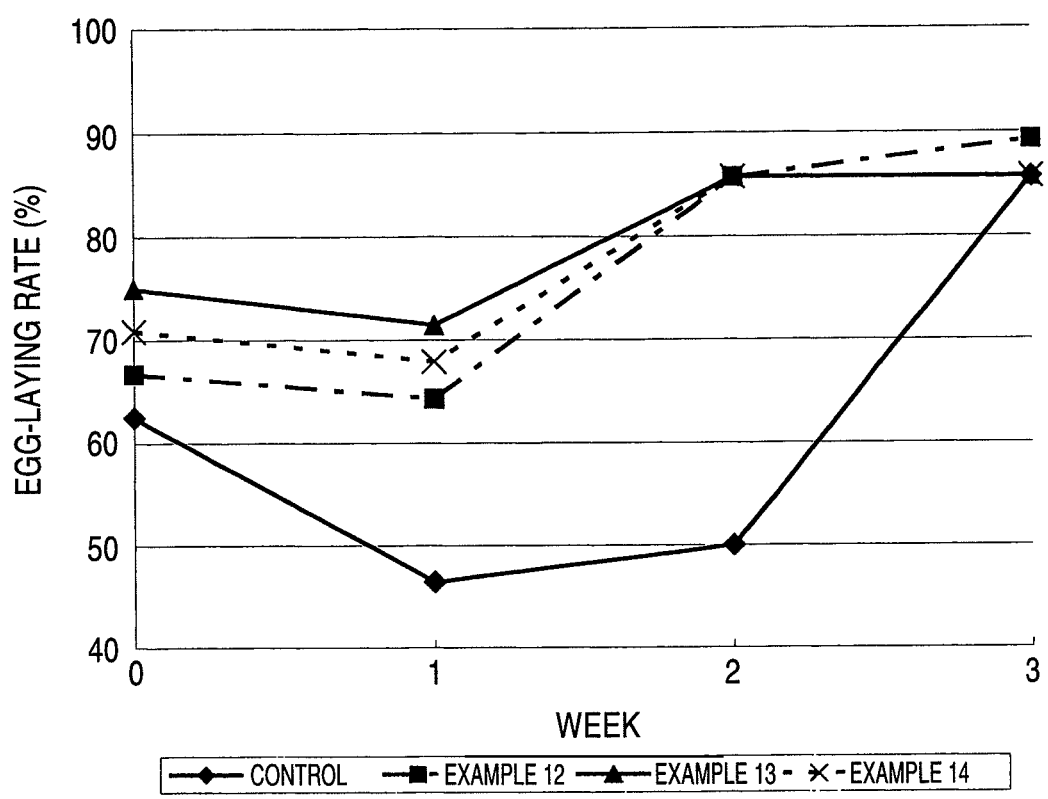

FEED ADDITIVE FOR LAYING HEN AND FEED CONTAINING THE SAME

This application is a Divisional of U.S. application Ser. No. 10/587,945, filed Aug. 2, 2006; which is a 371 of PCT/JP05/001592 filed Feb. 3, 2005; the entire disclosures of each of which are incorporated herein by reference.

TECHNICAL FIELD

This invention relates to a feed additive for laying hens and a feed containing the same. More specifically, it relates to a feed additive having an effect of reinforcing eggshells and a feed containing the same.

BACKGROUND ART

Bird eggs such as chicken eggs are highly nutritious foods containing various nutritional components. Moreover, eggs are highly suitable for cooking. Owing to these characteristics, eggs are very important food resources. In the process of delivering newly laid eggs to consumers, however, eggshells are sometimes broken (egg breakage) or finely cracked (egg cracking). These broken eggs and cracked eggs have little or no commercial value, which causes an increase in the cost. Owing to the introduction of automatic detectors, the rate of eliminating cracked eggs, which used to range from 7 to 8%, attains 12 to 15% in these days and puts serious pressure on egg farmers' profits.

It is considered that egg breakage and egg cracking arise since eggshells are weakened because of stress or failure in calcium utilization and so on. Calcium participating in eggshell formation is mainly supplied by feeds. Therefore, it is well known that calcium insufficiency in a feed results in thinning and weakening in eggshells.

To overcome the problems of egg breakage and egg cracking, there have been employed methods of 1) shortening the egg collection period; 2) forced molting (stop laying by fasting); and 3) administering an eggshell reinforcing agent.

Examples of the eggshell reinforcing agent as described above in 3) include beef meat-and-bone meal serving as a calcium source, calcium carbonate, CPP (casein phosphopeptide) capable of increasing the absorptivity of calcium (see Patent Document 1), an eggshell reinforcing agent comprising crab shell for reinforcing an eggshell per se together with chitosan, etc. for strengthening the eggshell membrane supporting the eggshell (see Patent Document 2). In addition, there have been known a feed containing poly-γ-glutamic acid (see Patent Document 3) and an eggshell reinforcing agent comprising trehalose (see Patent Document 4).

On the other hand, lactobionic acid represented by O-β-D-galactopyranosyl-(1-4)-D-gluconic acid has been already approved by FDA and added to pudding premixes as a solidifying agent or employed in cosmetics as a humidifier in the United States. Concerning functions, it has been reported that lactobionic acid shows activities of selectively stimulate the proliferation of bifid bacteria (see Patent Document 5) and stimulating mineral absorption (see Patent Document 6). It has been also reported that the administration of a chelate composed of lactobionic acid, iron and copper resulted in an increase in the hemoglobin level and improvement in anemia (see Non-patent Document 1). However, it has never been known that lactobionic acid has an effect of reinforcing eggshells.

Patent Document 1: JP-A-1-285158
Patent Document 2: JP-A-9-47232
Patent Document 3: JP-A-9-28309
Patent Document 4: JP-A-2001-95499
Patent Document 5: JP-A-7-277990
Patent Document 6: JP-A-7-277991
Non-patent Document 1: The American Journal of Clinical Nutrition, 1982, Vol. 36, No. 6, p. 1162 to 1169

DISCLOSURE OF THE INVENTION

Problems that the Invention is to Solve

However, the forced molting 2) suffers from a problem from the viewpoint of animal protection. Moreover, it is reported that forced molting induces salmonella infection, which brings about another problem of worsening safety of chicken eggs. Furthermore, there arises an additional problem that the egg-laying rate is lowered due to stress caused by forced molting, cage transfer, etc.

The existing eggshell reinforcing agents 3) suffer from a problem that their effects would lower in the second half of the laying period.

An object of the present invention is to provide a feed additive for laying hens, which is excellent in effect of reinforcing eggshells and expected as showing a particularly remarkable effect of improving eggshell qualities in the second half of the laying period, relieves stress caused by forced molting, cage transfer and so on and can inhibit lowering in the egg-laying rate.

Means for Solving the Problems

To achieve the above-described object, the inventors conducted intensive studies. As a result, they have found out that lactobionic acid, which is represented by a general formula O-β-D-galactopyranosyl-(1-4)-D-gluconic acid, or its salt can remarkably reinforce eggshells, thereby completing the present invention.

Accordingly, the gist of the invention resides in a feed additive for laying hens which comprises lactobionic acid or its salt. In another embodiment, the gist of the invention resides in a feed characterized by containing a feed additive for laying hens comprising lactobionic acid or its salt.

Effect of the Invention

According to the present invention, eggshells of chicken eggs and so on can be reinforced and thus the egg breakage rate and the egg cracking rate can be lowered. It is also possible to lessen fecal odor of chickens etc. Moreover, it is possible to relieve stress due to cage transfer, forced molting, etc. and improve the egg-laying rate, the egg qualities and the eggshell qualities.

BRIEF DESCRIPTION OF DRAWING

FIG. 1 shows changes in egg-laying rate with the passage of time.

BEST MODE FOR CARRYING OUT THE INVENTION

Now, the present invention will be described in greater detail.

Lactobionic acid to be used in the present invention, which is represented by a general formula O-β-D-galactopyranosyl-(1-4)-D-gluconic acid, can be obtained by oxidizing lactose. More specifically, it can be obtained by treating lactose as the substrate with a microorganism having a lactose dehydrogenase activity such as *Pseudomonas graveolens* or oxidizing lactose with bromine or the like. From the economical viewpoint, it is most advantageous to employ a method which comprises oxidizing lactose by oxidase acting on lactose as the substrate or a microorganism having this enzyme which belongs to the genus *Acinetobacter* or *Burkholderia* (see, in detail, JP-A-2001-245657).

The lactobionic acid salts usable in the invention include calcium salt, sodium salt, potassium salt, magnesium salt, iron salt, zinc salt, copper salt and so on. These salts can be prepared by conventional reaction methods for converting into salt such as neutralization. Among them, calcium salt can be also prepared by a method which comprises preliminarily adding calcium carbonate to a reaction system for producing lactobionic acid from lactose by a biological conversion method with the use of an enzyme or a microorganism. This method is more convenient.

In general, calcium cannot be absorbed unless it is in the soluble state in the intestinal tract. Because of having an extremely high solubility in water (>40 g/100 mL), calcium lactobionate is excellent in the calcium-supplying effect and usable as a calcium source for eggshells even in the absence of any other calcium sources.

Considering convenience in using, the feed additive for laying hens according to the invention, which comprises lactobionic acid or its salt as described above, can be obtained by processing them into a powder, an aqueous solution or compressed tablets to give a feed additive for laying hens.

By administering the feed additive for laying hens to chickens either directly or as a mixture with a feed for chickens or drinking water, it is possible to reinforce eggshells and lower the egg breakage rate and the egg cracking rate compared with the case of not administering the same. The feed additive for laying hens according to the invention may be administered to any birds without restriction. Thus, it is usable for quails, ducks and so on in addition to domestic fowl. That is to say, the term "laying hens" as used in the present invention involves quails, ducks and so on.

The feed according to the invention can be obtained by adding the feed additive for laying hens as described above to a basic feed.

The basic feed for chickens may be an arbitrary one commonly employed for a feed for chickens. For example, use can be made of those obtained by blending organic nutritional sources such as corn, milo, soybean meal, fish meal and wheat flour and inorganic nutritional sources such as sodium chloride, calcium phosphate and calcium carbonate with feed additives comprising trace elements such as vitamins, metals and antibiotics.

The feed additive for laying hens is added to the basic feed preferably in an amount of from 0.01 to 10% by weight, more preferably from 0.05 to 1% by weight and most desirably from 0.1 to 0.5% by weight. When the addition level is too low, it frequently takes a long time to achieve the desired effects. When the addition level is too high, there sometimes arise problems in nutritional balance or cost. In the case of adding lactobionic acid as the feed additive for laying hens, it is preferred to simultaneously add a calcium source such as calcium phosphate or calcium carbonate. In the case of adding calcium lactobionate as the feed additive for laying hens, it is not always necessary to add another calcium source.

The feed additive for laying hens may be added to a feed by any method without particular restriction. For example, use may be made of a method of adding as a powder as such, a method of adding as an aqueous solution, a method of adding as compressed tablets and so on. Similarly, no restriction is imposed on feed form (powder, solid), feeding method or feeding time (day age of laying hens).

It is preferable that the feed according to the invention is administered to laying hens in an amount of from 10 mg to 10 g per day in terms of the feed additive for laying hens contained therein, more preferably from 50 mg to 1.0 g and most desirably from 0.1 g to 0.5 g.

It has been also clarified that by administering the feed additive for laying hens to chickens either directly or as a mixture with a feed for chickens or drinking water, a secondary effect of considerably lessening the fecal odor can be achieved compared with the case of not administering the same. Fecal odor emitted from chicken farms is a serious problem at present. According to the Law on Promoting Proper Management and Use of Livestock Excreta, feces should be contained in a roofed warehouse provided with a cement floor and dried before shipping from the end of March, 2004 in Japan. Therefore, it seems urgently required to develop an agent for lessening fecal odor.

It is estimated that the effect of lessening fecal odor of the feed additive for laying hens according to the invention is caused by the function of lactobionic acid or its salt of controlling intestinal movements.

EXAMPLES

Now, the present invention will be illustrated in greater detail by referring the following Examples. However, it is to be understood that the invention is not restricted thereto.

Example 1

Preparation of Calcium Lactobionate

In 5 L of a 10 mM phosphate buffer solution (pH 7.0) containing 1000 g of lactose and 825 g of $CaCO_3$, 200 g of GRINGAMYL SURE BAKE 800 (manufactured by DANISCO, a recombinant enzyme of marine algae-origin hexose oxidase) was suspended to give a liquid reaction mixture. This liquid reaction mixture was allowed to react under stirring and aerating (blowing air at a rate of 0.5 times by volume as much as the liquid reaction mixture per minute) for 2 days at 30° C. Then, the liquid reaction mixture was centrifuged (10,000 rpm, 30 minutes at 4° C.) to thereby remove $CaCO_3$. The obtained supernatant was supplied into an active carbon column (5 cm (diameter)×40 cm) having been equilibrated with deionized water and eluted with 1500 ml of deionized water. The eluate was collected, concentrated to 300 mL under reduced pressure and then precipitated by adding ethanol 2.3 times as much. The precipitate was dried under reduced pressure to thereby give 1020 g of calcium lactobionate.

As the results of HPLC analysis (column: Asahipak $NH_2P$-50 (manufactured by Shodex), eluent: acetonitrile/40 mM citric acid-$NaH_2PO_4$ buffer (pH 5.0)=60/40 (ratio by volume), temperature: 40° C., flow rate: 0.8 ml/min, detector: differential refractometer (Waters 410: manufactured by Waters)) on the lactobionic acid, no elution peak assignable to impurities was found out, which indicated that the obtained product was highly pure lactobionic acid. The solubility in water of the calcium lactobionate thus obtained was compared with those of other calcium salts (manufactured by Wako Pure Chemical Industries). Table 1 shows the results. Thus, it can be understood that calcium lactobionate has a much higher solubility in water than other calcium salts.

TABLE 1

| Solubilities in water of various calcium salts (g/100 mL) | | | | | |
|---|---|---|---|---|---|
| Ca oxalate | 0.001 | Ca diphosphate | 0.03 | Ca gluconate | 3.8 |
| Ca carbonate | 0.0014 | Ca citrate | 0.96 | Ca lactobionate | >40 |

Examples 2 to 5

Preparation of Feed

To a basic feed for laying hens having the composition as listed in Table 2, calcium lactobionate prepared in Example 1 was added at concentrations of 0.05, 0.1, 1.0 and 2.0% by weight to give feeds which were referred to respectively as Examples 2 to 5.

TABLE 2

| Composition of basic feed (%) | |
|---|---|
| Starting material | Content (%) |
| Yellow corn | 69.4 |
| Soybean meal | 16.0 |
| CP65% fish meal | 3.0 |
| Alfalfa meal | 2.0 |
| DL-Methionine | 0.1 |
| L-Lysine hydrochloride | 0.1 |
| Calcium carbonate | 6.5 |
| Di-lime phosphate | 2.0 |
| Sodium chloride | 0.3 |
| Premix of inorganic trace elements[1] | 0.2 |
| Premix of vitamins A, D and E[2] | 0.2 |
| Premix of vitamin B family[3] | 0.2 |
| Total | 100 |

[1] Containing 80 g of Mn, 50 g of Zn, 6 g of Fe, 0.6 g of Cu and 1 g of I per kg
[2] Containing 10,000 IU of vitamin A, 2,000 IU of vitamin $D_3$ and 20 mg of vitamin E per g.
[3] containing 2.0 g of thiamine nitrate, 10.0 g of riboflavin, 2.0 of pyridoxine hydrochloride, 2.0 g of nicotinamide, 4.35 g of calcium D-pantothenate, 138.0 g choline chloride and 1.0 g of folic acid per kg.

Test Example 1

Ten laying hens aged 470 days (laying white leghorn hens (Julia)) were fed with each of the feeds prepared in Examples 2 to 5 for 60 days and the egg-laying rate, the egg breakage and egg cracking rate and eggshell strength were measured. The egg-laying rate was determined in accordance with the following Equation 1, while the egg breakage and egg cracking rate were determined in accordance with the following Equation 2. Eggshell strength was determined by horizontally placing an egg and measuring the bursting strength with a rheometer. A feed containing no feed additive for laying hens was also prepared as a control. During the test period, no chicken died. Table 3 summarizes the results.

Egg-laying rate=(total number of eggs in each test lot/total number of eggs in control lot)×100 [Equation 1]

Egg breakage/cracking rate=(number of broken or cracked eggs/total number of eggs yield)×100 [Equation 2]

TABLE 3

| Test lot | Addition level (%) of feed additive | Egg-laying rate (%) | Egg breakage/ cracking rate (%) | Eggshell strength (kg/cm²) |
|---|---|---|---|---|
| Control | 0 | 100 | 7.3 | 2.8 |
| Ex. 2 | 0.05 | 100.3 | 5.0 | 3.2 |
| Ex. 3 | 0.1 | 99.1 | 3.2 | 3.8 |
| Ex. 4 | 1.0 | 100.5 | 2.0 | 3.9 |
| Ex. 5 | 2.0 | 101.0 | 1.8 | 4.1 |

As the results given in Table 3 indicate, each of the test lots of Examples 2 to 5 showed no difference in the egg-laying rate from the control lot but an obvious decrease in the egg breakage and egg cracking rate and an improvement in the eggshell strength. Each of the test lots of Examples 2 to 5 showed no difference in the egg weight from the control lot. In each of the test lots of Examples 2 to 5, fecal odor was lessened and this tendency was particularly remarkable in the test lots of Examples 4 and 5.

Examples 6 to 9

Preparation of Feed

To the basic feed for laying hens having the composition as shown in Table 2, lactobionic acid (manufactured by Wako Pure Chemical Industries) was added at concentrations of 0.05, 0.1, 1.0 and 2.0% by weight to give feeds which were referred to respectively as Examples 6 to 9.

Test Example 2

Ten laying hens aged 280 days (laying white leghorn hens (Julia)) were fed with each of the feeds prepared in Examples 6 to 9 for 70 days and the egg-laying rate, the egg breakage and egg cracking rate and eggshell strength were measured in the same manner as in Examples 2 to 5. During the test period, no chicken died. Table 4 summarizes the results.

TABLE 4

| Test lot | Addition level (%) of feed additive | Egg-laying rate (%) | Egg breakage/ cracking rate (%) | Eggshell strength (kg/cm²) |
|---|---|---|---|---|
| Control | 0 | 100 | 5.0 | 3.2 |
| Ex. 6 | 0.05 | 99.6 | 3.4 | 3.8 |
| Ex. 7 | 0.1 | 101.2 | 2.2 | 3.8 |
| Ex. 8 | 1.0 | 99.2 | 2.0 | 4.0 |
| Ex. 9 | 2.0 | 100.7 | 2.3 | 4.1 |

As the results given in Table 4 indicate, each of the test lots of Examples 6 to 9 showed no difference in the egg-laying rate from the control lot but an obvious decrease in the egg breakage and egg cracking rate and an improvement in the eggshell strength. Each of the test lots of Examples 6 to 9 showed no difference in the egg weight from the control lot. In each of the test lots of Examples 6 to 9, fecal odor was lessened and this tendency was particularly remarkable in the test lots of Examples 8 and 9.

Examples 10 and 11

From the composition of the basic feed for laying hens as shown in Table 2, calcium carbonate and di-lime phosphate were removed. To the obtained feed, calcium lactobionate prepared in Example 1 was added at concentrations of 1.0 and 2.0% by weight to give feeds which were referred to respectively as Examples 10 and 11.

Test Example 3

Ten laying hens aged 470 days (laying white leghorn hens (Julia)) were fed with each of the feeds prepared in Examples 10 and 11 for 60 days and the egg-laying rate, the egg breakage and egg cracking rate and eggshell strength were measured in the same manner as in Examples 2 to 5. During the test period, no chicken died. Table 5 summarizes the results.

TABLE 5

| Test lot | Addition level (%) of feed additive | Egg-laying rate (%) | Egg breakage/ cracking rate (%) | Eggshell strength (kg/cm$^2$) |
|---|---|---|---|---|
| Control | 0 | 100 | 7.3 | 2.8 |
| Ex. 10 | 1.0 | 100.8 | 2.1 | 4.0 |
| Ex. 11 | 2.0 | 100.5 | 1.9 | 4.1 |

As the results given in Table 5 indicate, each of the test lots of Examples 10 and 11 showed no difference in the egg-laying rate from the control lot but an obvious decrease in the egg breakage and egg cracking rate and an improvement in the eggshell strength. Accordingly, it was clarified that calcium lactobionate alone showed an effect of reinforcing eggshells even in the case of adding no calcium source except calcium lactobionate to feeds. Each of the test lots of Examples 10 and 11 showed no difference in the egg weight from the control lot. In Examples 9 and 10, fecal odor was remarkably lessened.

Examples 12 to 14

Preparation of Feed

To the basic feed for laying hens having the composition as shown in Table 2, calcium lactobionate was added at concentrations of 0.1, 0.5 and 1.0% by weight to give feeds which were referred to respectively as Examples 12 to 14.

Test Example 4

Four laying hens aged 500 days (Boris Brown) were fed with each of the feeds prepared in Examples 12 to 14 for 60 days and the egg-laying rate and the eggshell strength were measured in the same manner as in Examples 2 to 5. During the test period, no chicken died. Table 6 summarizes the results.

TABLE 6

| Test lot | Addition level (%) of feed additive | Egg-laying rate (%) | Eggshell strength (kg/cm$^2$) |
|---|---|---|---|
| Control | 0 | 100 | 2.09 |
| Ex. 12 | 0.1 | 113 | 2.36 |
| Ex. 13 | 0.5 | 112 | 2.28 |
| Ex. 14 | 1.0 | 103 | 2.53 |

As the results given in Table 6 indicate, each of the test lots of Examples 12 to 14 showed an obvious improvement in the eggshell strength. Thus, it was clarified that an eggshell reinforcing effect could be obtained by adding calcium lactobionate to a feed. Each of the test lots of Examples 12 to 14 showed no difference in the egg weight from the control lot.

Test Example 5

Four laying hens aged 500 days (Boris Brown) were fed with each of the feeds prepared in Examples 12 to 14 for 9 weeks. Feces of the laying hens were collected every week. The feces were suspended in 10 times as much distilled water and acetic acid contained in the supernatant was quantified by HPLC. Namely, the samples were analyzed by HPLC conducted under the following conditions: column: Aminex HPX 87H (300×7.8 mm (diameter), manufactured by BIORAD), column temperature: 60° C., developing solvent: 0.005 N sulfuric acid, sample amount: 30 μl, flow rate: 0.6 ml/min, detector: RI. Table 7 summarizes the results.

TABLE 7

| | Amount of acetic acid in feces | |
|---|---|---|
| Lot | Addition level (%) of feed additive | Acetic acid content (μg/mg) |
| Control | 0.0 | 1.12 ± 0.81 |
| Ex. 12 | 0.1 | 1.93 ± 1.74 |
| Ex. 13 | 0.5 | 1.41 ± 0.85 |
| Ex. 14 | 1.0 | 2.42 ± 1.26 |

As the results given in Table 7 indicate, the acetic acid content was increased in each of the test lots of Examples 12 to 14 compared with the control lot. This is seemingly because calcium lactobionate was metabolized by intestinal bacteria and thus promoted the proliferation thereof to thereby enhance acetic acid production by the intestinal bacteria. It appears that the intestinal bacteria in the laying hens were increased by the administration of calcium lactobionate and thus the intestinal environment was improved, which resulted in the lessening in the fecal odor.

Test Example 6

Four laying hens aged 500 days (Boris Brown) were fed with each of the feeds prepared in Examples 12 to 14 for 3 weeks after cage transfer. Then the egg-laying rates were calculated. FIG. 1 summarizes the results.

As the results given in FIG. 1 indicate, a lowering in egg-laying rate due to cage transfer was observed in the control lot, while each of the test lots of Examples 12 to 14 showed a higher egg-laying rate than the control lot. This is seemingly because the stress loaded on the laying hens was relieved by calcium lactobionate.

While the present invention and specific modes for the embodiment thereof have been described in detail, it is obvious for those skilled in the art that various alterations and modifications can be made without departing from the spirit and scope of the invention.

The present application is based on Japanese Patent Application filed on Feb. 6, 2004 (Japanese Patent Application No. 2004-030898) and the contents thereof are employed herein as reference.

INDUSTRIAL APPLICABILITY

According to the present invention, it is possible to provide a feed additive for laying hens which is excellent in effect of reinforcing eggshells, shows a particularly remarkable effect of improving eggshell qualities in the second half of the laying period, relieves stress caused by forced molting, cage transfer and so on and can inhibit lowering in the egg-laying rate.

The invention claimed is:

1. A method of reinforcing eggshells of eggs laid by hens, which comprises the step of administering to an egg-laying hen in need thereof an effective amount of lactobionic acid or an inorganic salt thereof.

2. A method of relieving stress on laying hens, which comprises the step of administering to an egg-laying hen in need thereof an effective amount of lactobionic acid or an inorganic salt thereof.

3. A method of inhibiting lowering in egg-laying rate in laying hens, which comprises the step of administering to an egg-laying hen in need thereof an effective amount of lactobionic acid or an inorganic salt thereof.

4. The method according to claim 1, wherein the inorganic salt is at least one selected from the group consisting of calcium salt, sodium salt, potassium salt, magnesium salt, iron salt, zinc salt and copper salt.

5. The method according to claim 1, wherein the inorganic salt is calcium lactobionate.

6. The method according to claim 2, wherein the inorganic salt is at least one selected from the group consisting of calcium salt, sodium salt, potassium salt, magnesium salt, iron salt, zinc salt and copper salt.

7. The method according to claim 2, wherein the inorganic salt is calcium lactobionate.

8. The method according to claim 3, wherein the inorganic salt is at least one selected from the group consisting of calcium salt, sodium salt, potassium salt, magnesium salt, iron salt, zinc salt and copper salt.

9. The method according to claim 3, wherein the inorganic salt is calcium lactobionate.

* * * * *